Figure 1:
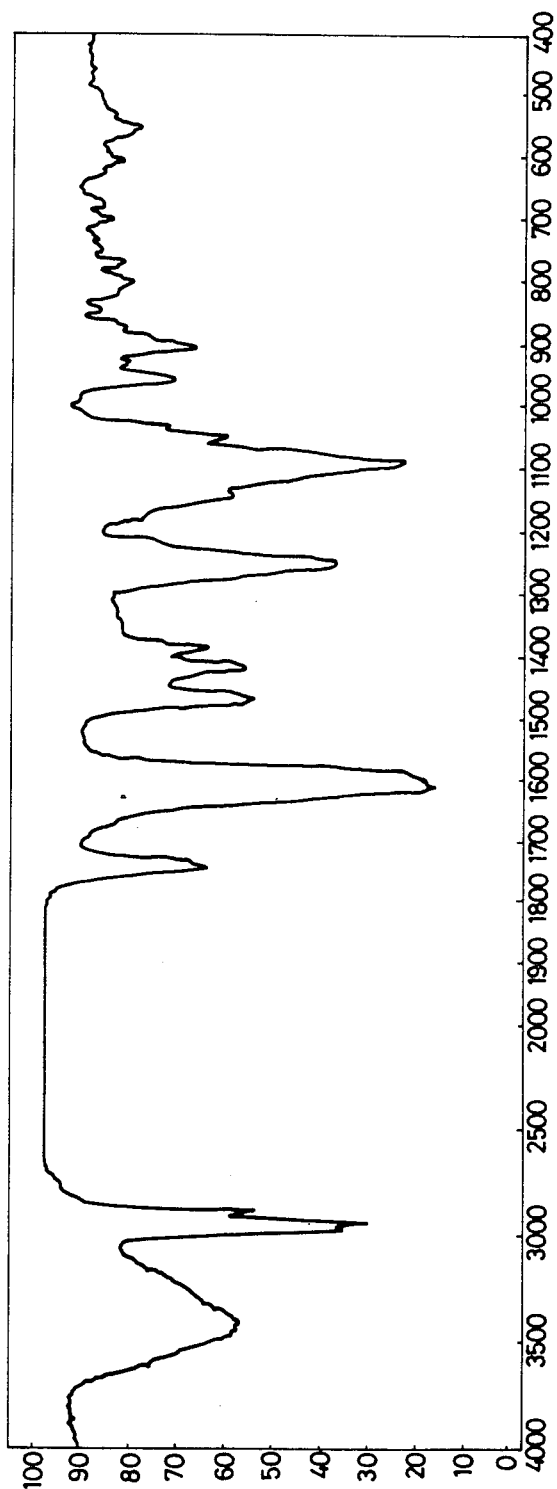

United States Patent [19]

Ogata

[11] Patent Number: 4,564,686
[45] Date of Patent: Jan. 14, 1986

[54] PHOSPHORIC ACID DIESTERS OR THEIR SALTS AND PROCESS FOR PRODUCING THE SAME

[75] Inventor: Kazumi Ogata, Toyonaka, Japan

[73] Assignee: Senju Pharmaceutical Co., Ltd., Osaka, Japan

[21] Appl. No.: 615,308

[22] Filed: May 30, 1984

[30] Foreign Application Priority Data

May 30, 1983 [JP] Japan .................................. 58-96428

[51] Int. Cl.[4] ............................ C07F 9/06; C07F 9/28
[52] U.S. Cl. ................................................. 549/220
[58] Field of Search ................. 549/408, 220; 424/203

[56] References Cited

U.S. PATENT DOCUMENTS

| | | | |
|---|---|---|---|
| 3,064,009 | 11/1962 | Rigterink et al. | 424/203 |
| 3,067,210 | 12/1962 | Schrader | 424/203 |
| 3,294,630 | 12/1966 | Poll et al. | 424/203 |
| 3,294,636 | 12/1966 | Brown et al. | 424/203 |
| 4,303,653 | 12/1981 | Chiyomaru et al. | 424/203 |

FOREIGN PATENT DOCUMENTS 0127471 12/1984 European Pat. Off. ............ 549/220

*Primary Examiner*—Ethel G. Love
*Attorney, Agent, or Firm*—Burgess, Ryan & Wayne

[57] ABSTRACT

A phosphoric acid diester of the formula:

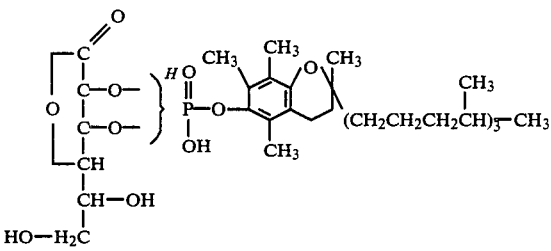

or its salt is produced by reacting α-tocopherol with a halogenophosphorylating agent and reacting the resulted product with ascorbic acid having protected hydroxy groups in the 5- and 6-positions followed by removing the protected groups. The compound can be employed as prophylactic and therapeutic agents for cataracts and climacteric hazards and also as an ingredient for cosmetics having skin-beautifying action.

13 Claims, 2 Drawing Figures

PHOSPHORIC ACID DIESTERS OR THEIR SALTS AND PROCESS FOR PRODUCING THE SAME

The present invention relates to novel phosphoric acid diesters or their salts and a process for producing the same.

The phosphoric acid diesters of the present invention have the structure in which out of three hydroxyl groups of phosphoric acid, two are esterified with one hydroxyl group each of α-tocopherol and ascorbic acid, respectively.

Ascorbic acid is the antiscurvy agent and suppresses the deposit of melanin which is attributable to liver-spot and ephelis. Moreover, it has been recently said to exhibit an anti-cancer effect.

On the other hand, α-tocopherol does not exhibit directly an anti-cancer action, but it is said that those having the daily intake of α-tocopherol are less susceptible to attack by cancer. In addition, α-tocopherol is regarded as effective against the climacteric hazards such as numbness of hands and feet, and like ascorbic acid, is also concerned in the oxidation-reduction in the living body, which suggests in recent years that it is effective for the treatment of cataracts.

The compound having ascorbic acid and α-tocopherol being linked through phosphoric acid has not been known so far. The present inventor, after repeated intensive research, succeeded in the synthesis of the compounds of the present invention that comprise 1 mole each of ascorbic acid and α-tocopherol being linked to 1 mole of phosphoric acid in the diester form.

The compounds of the present invention are considered to have the structure as represented by the following formula [I].

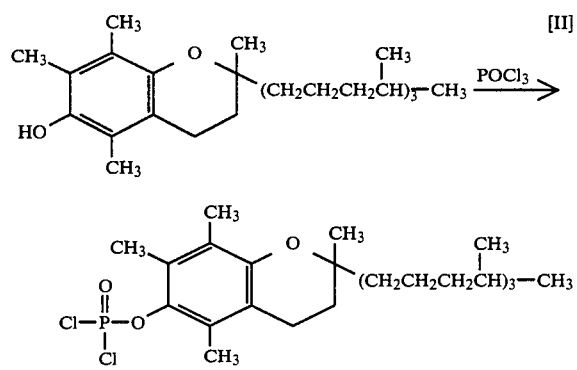

The product (designated by [II] in the above formula) as obtained by the above procedure is reacted with ascorbic acid having the hydroxyl groups in the 5- and 6-positions protected with protecting groups. With reference to the protecting groups for the hydroxyl groups in the 5- and 6-positions of ascorbic acid, proper selection can be made out of various protecting groups which are known in the field of synthesis of ascorbic acid, and the most common isopropylidene group can be employed in the process according to the present invention, as well. The reaction proceeds in such a solvent as tetrahydrofuran in the presence of a deacidifying agent such as pyridine. Subsequently, the protecting groups are eliminated from the reaction product. This reaction is carried out through hydrolysis under mild conditions, for example, by the use of 1N hydrochloric acid. Even when a halogenophosphoric acid group is present in the above-mentioned reaction product, it can be converted into a phosphoric acid group by

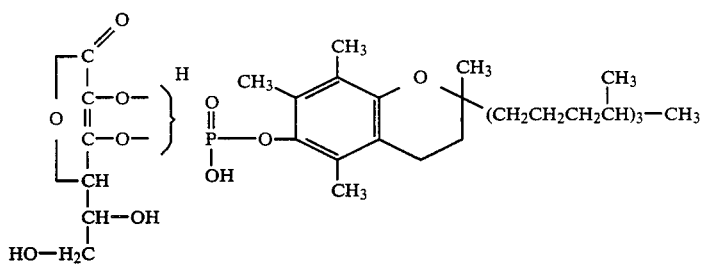

The present invention is concerned with phosphoric acid diesters of the formula [I] or their salts, and with a process for producing phosphoric acid diesters of the formula [I] or their salts, characterized in that said process comprises reacting α-tocopherol with a halogenophosphorylating agent, and reacting the resultant product with ascorbic acid having the hydroxyl groups in the 5- and 6-positions protected with protecting groups, followed by removal of the above-mentioned protecting groups.

In the process according to the present invention, a halogenophosphorylating agent is acted on α-tocopherol. Preferred examples of the halogenophosphorylating agent include phosphorus oxytrichloride, phosphorus oxytribromide, etc. The reaction proceeds readily in such a non-reactive solvent as benzene in the presence of a deacidifying agent, for example, pyridine. When phosphorus oxytrichloride is employed as the halogenophosphorylating agent, the reaction formula is illustrated in the following manner.

changing its halogens to hydroxyl groups simultaneously with the removal of the protecting groups in the above-mentioned hydrolysis.

By the above procedure, there is obtained the compound [I].

The compounds of the present invention are more crystalline in the form of salts than as free acids. Their salts, such as sodium and potassium salts, are highly soluble in water, whereas their calcium salts, for example, are insoluble. Therefore, the type of salts can be selected according to the purpose.

In order to convert their free acids into alkali salts, in general, it is preferable to neutralize with alkali hydroxides.

Figure 2:
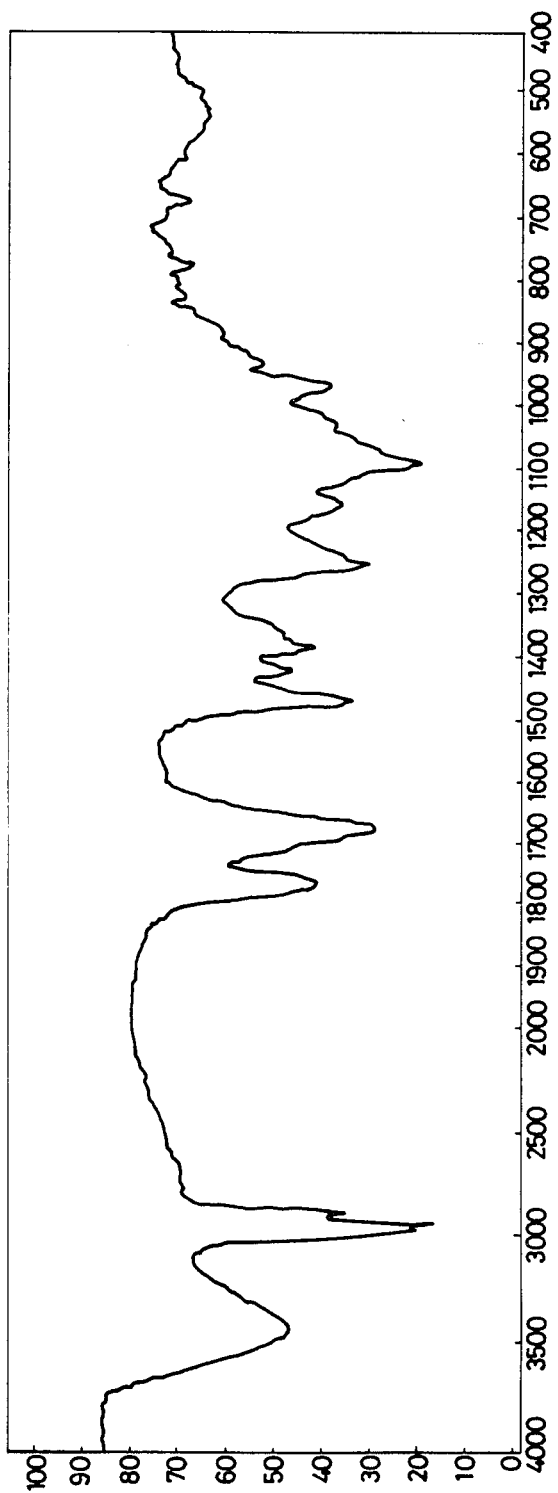

In the drawings, FIGS. 1 and 2 show the infrared adsorption spectra of the potassium salt and free acid of the compound of the present invention, respectively.

The compounds of the present invention, either in the form of free acid or suitable salt, can be processed into various pharmaceutical preparations, such as injections, collyria, tablets and capsules, by known procedures.

The compounds of the present invention do not have the reducing action and are therefore stable in the air. Yet, they restore readily the reducing action, for example, when heated with hydrochloric acid. Consequently, they can be administered to the living body as stable pharmaceutical preparations, and at the same time, can be expected to develop the actions of Vitamins C and E in the body through splitting off of the phosphoric acid esters by the action of phosphatase, etc.

Also, the compounds of the present invention, in the form of salts such as sodium and potassium salts, exhibit enhanced solubility in water, and are free of the defects such as turbidity appearing in the neighborhood of the neutral pH and precipitate formation through addition of sodium chloride, as is the case with the phosphoric acid ester of α-tocopherol.

The compounds of the present invention are, for example, used as prophylactic and therapeutic agents for cataracts and climacteric hazards, and also employed as an ingredient for cosmetics such as those having a skin-beautifying action.

The examples are described below to illustrate the present invention.

EXAMPLE 1

L-ascorbic acid, DL-α-tocopherol phosphoric acid ester potassium salt.

In 50 ml of benzene is dissolved 6.12 g of phosphorus oxytrichloride, and a solution mixture of 8.6 g (0.02 mole) of DL-α-tocopherol and 9.5 g of pyridine in 50 ml of benzene is added dropwise to the solution under stirring. After the dropwise addition is completed, stirring is continued for another 3 hours, and the precipitating pyridine hydrochloride is filtered out. The filtrate is concentrated under reduced pressure, and 30 ml of benzene is added to the resultant residual, oily substance.

5.2 g (0.024 mole) of 5,6-isopropylideneascorbic acid resulting from the acetonation of L-ascorbic acid and 3.2 g of pyridine are dissolved in 120 ml of tetrahydrofuran (THF), and the solution is added dropwise to the above benzene solution. After the dropwise addition is completed, stirring is continued for about 1 hour, and the precipitating pyridine hydrochloride is filtered out, whereby the filtrate is freed of the solvent under reduced pressure. The resultant oily substance is dissolved in 30 ml of ethyl alcohol, and 150 ml of 1N hydrochloric acid is added to the solution, followed by heating under reflux for about 20 minutes. The solution is cooled, and extraction is conducted with ethyl acetate. The organic layer is dried over anhydrous sodium sulfate and the ethyl acetate is distilled off. There is obtained a crude free acid as a residue.

The crude free acid is dissolved in about 100 ml of ethyl alcohol, and a solution of potassium hydroxide in ethyl alcohol is gradually added dropwise to the solution until the pH of the solution becomes neutral, whereby slightly brown-tinged white crystals separate out. The crystals are recovered by filtration and recrystallized from water-ethyl alcohol-acetone to yield 7.5 g of white powder crystals.

Melting point: Carbonization gradually begins at temperature in the neighborhood of 210° C.

Ultraviolet absorption spectrum (UV): It shows an absorption maximum in the neighborhood of 257 nm (in water).

Silica-gel thin-layer chromatography: Rf=8.1 (ethyl alcohol:acetone:water=10:4:1).

Elemental analysis, for $C_{35}H_{55}O_{10}PK_2 \cdot H_2O$. Calcd.: C, 55.09%; H, 7.53%. Found: C, 55.32%; H, 7.65%.

Infrared absorption spectrum (KBr disk): As is shown in FIG. 1.

EXAMPLE 2

L-ascorbic acid, DL-α-tocopherol phosphoric acid ester sodium salt.

In 30 ml of water is dissolved 5 g of the L-ascorbic acid-DL-α-tocopherol phosphoric acid ester potassium salt as obtained in Example 1, and the solution is made acidic by the addition of hydrochloric acid. After the extraction with ethyl acetate, the organic layer is freed of the ethyl acetate to yield the free acid of L-ascorbic acid-DL-α-tocopherol phosphoric acid ester (the absorption maximum of the UV spectrum is at 285 nm, in water). The infrared absorption spectrum is shown in FIG. 2. The free acid is dissolved in ethyl alcohol, and a 30% aqueous sodium hydroxide solution is gradually added to the solution until the solution becomes neutral, whereby there are obtained white crystals. The crystals are recovered by filtration, washed with ethyl alcohol and dried to give about 4 g of the subject compound.

Elemental analysis, for $C_{35}H_{55}O_{10}PNa_2 \cdot H_2O$. Calcd.: C, 57.52%; H, 7.86%. Found: C, 57.65%; H, 7.98%.

EXAMPLE 3

L-ascorbic acid, DL-α-tocopherol phosphoric acid ester calcium salt

In 100 ml of water is dissolved 5 g of the potassium salt as obtained in Example 1, and 2 g of calcium chloride is added to the solution, whereby the precipitating white crystals are recovered by filtration, washed with water and dried to yield about 4.5 g of the subject compound.

Elemental analysis, for $C_{35}H_{55}O_{10}PCa \cdot H_2O$. Calcd.: C, 57.99%; H, 7.93%. Found: C, 58.12%; H, 8.22%.

EXAMPLE 4

L-ascorbic acid, D-α-tocopherol phosphoric acid ester potassium salt.

D-α-tocopherol acetate (produced by Amakasu Chemical Co. of Japan) is heated in a mixed solution of 50% aqueous sulfuric acid and ethyl alcohol (the ratio of about 1:5) to conduct hydrolysis. With the use of D-α-tocopherol thus obtained, treatment is carried out in the same manner as in Example 1.

By the above procedure, there is obtained 7.5 g of slightly brown tinged white powder crystals. $[\alpha]_D^{23} + 40.3°$ (c=1, $H_2O$).

PREPARATION EXAMPLE 1

Injections

| | |
|---|---|
| L-ascorbic acid, D-α-tocopherol phosphoric acid ester potassium salt | 0.2 g |
| Glucose | 5 g |

The above ingredients are dissolved in distilled water for injection, and the solution is adjusted to pH 6.8 with 1N hydrochloric acid and made up to 100 ml of the total volume with distilled water. The solution is filtered, and 2 ml each of the filtrate is filled under sterile conditions into glass ampoules, which are then sealed to provide injectable compositions.

PREPARATION EXAMPLE 2

Collyria

| | |
|---|---|
| L-ascorbic acid, DL-α-tocopherol phosphoric acid ester potassium salt | 0.5 g |
| Boric acid | 1.8 g |
| Benzalkonium chloride | 0.005 g |

The above ingredients are dissolved in sterilized, purified water, and the solution is adjusted to pH 7.3 with 1N sodium hydroxide and made up to 100 ml of the total volume to provide a collyrium.

PREPARATION EXAMPLE 3

Tablets

| | |
|---|---|
| L-ascorbic acid, DL-α-tocopherol phosphoric acid ester calcium salt | 100 mg |
| Lactose | 80 mg |
| Starch | 17 mg |
| Magnesium stearate | 3 mg |

The above ingredients, as a raw material for one tablet, are molded into a tablet by the conventional method. The tablet may be coated with sugar, if necessary.

PREPARATION EXAMPLE 4

Syrup

| | |
|---|---|
| L-ascorbic acid, DL-α-tocopherol phosphoric acid ester potassium salt | 2.0 g |
| 70% aqueous solution of D-sorbitol | 70 ml |
| Methyl p-hydroxybenzoate | 0.025 g |
| Butyl p-hydroxybenzoate | 0.012 g |

The above ingrdients are dissolved in sterilized, purified water. The solution is adjusted to pH 6.0 with 1N hydrochloric acid, made up to 100 ml of the total volume and filtered into a glass bottle to provide a syrup preparation.

PREPARATION EXAMPLE 5

Lotion

| | |
|---|---|
| L-ascorbic acid, DL-α-tocopherol phosphoric acid ester potassium salt | 1.0 g |
| Citric acid | 0.1 g |
| Glycerin | 5.0 g |
| Ethyl alcohol | 8.0 ml |
| Methyl p-hydroxybenzoate | 0.1 g |

The above ingredients are dissolved in sterilized, purified water. The solution is adjusted to pH 6.0 with 1N sodium hydroxid, made up to 100 ml of the total volume and filled into a glass bottle to provide a lotion.

PREPARATION EXAMPLE 6

Cream

| | |
|---|---|
| L-ascorbic acid, DL-α-tocopherol phosphoric acid ester potassium salt | 1.0 g |
| Stearic acid | 2.0 g |
| Stearyl alcohol | 7.0 g |
| Squalane | 5.0 g |
| Octyldodecanol | 6.0 g |
| Cetyl polyoxyethylene (15) ether | 3.0 g |
| Glycerin monostearate | 2.0 g |
| Methyl p-hydroxybenzoate | 0.2 g |
| Propyl p-hydroxybenzoate | 0.1 g |
| Sterilized, purified water | 68.7 g |

Propylene glycol and L-ascorbic acid, DL-α-tocopherol phosphoric acid ester potassium salt are added and dissolved into sterilized, purified water. The solution is heated to 70° C. While, the other ingredients are mixed each other, melted by heating and maintained at 70° C. The above-mentioned aqueous solution is added to the melted ingredients. The admixture is emulsified homogeneously and cooled to room temperature to provide a toiletary cream which is filled into a vessel for use in creams.

REFERENCIAL EXPERIMENT

If the present compound is hydrolyzed in living body to liberate vitamin E, the residue of the compound is to be the phosphate of vitamin C which is, as already known, readily converted to vitamin C (v. C) by phosphatase in the body. Therefore, the conversion of the present compound to vitamins E and C in living body can be proved by detecting vitamin E (v. E) in v. E deficient animals administered with the compound.

From the reason mentioned above, the compound prepared in Example 1 was administered to v. E deficient rats. Increase in the concentration of v. E in blood serum as well as the hemolysis of red blood cell were obserbed with the rats. No difference was observed as compared the rats with a group of rats administered with v. E. It proves the fact that the present compound converts to v. E in the animal body showing indirectly the conversion of the residual phosphate to v. C. The data are shown in the following:

Experimental animals: Male Wister rats, aged 4 weeks.

Method: Each of the present compound and vitamin E in the same moles are added to v. E-free diet (A) to make diets, (B) and (C).

| Diets | |
|---|---|
| (A) | V. E-free diet |
| (B) | (A) + present compound (761 mg/Kg in diet) |
| (C) | (A) + V. E (500 mg/Kg in diet) |

Respective diets, (A), (B) and (C) were administered to three groups of the rats respectively for 32 days and the blood of the each rat was collected. V. E concentration in blood plasma and hemolysis rate with dialuric acid were determined. The results are shown in Table 1.

TABLE 1

V. E concentration in blood plasma and hemolysis rate

| Diets | V. E μg/ml | Hemolysis rate (%) |
|---|---|---|
| (A) | 3.17 | 99.5 |
| (A) | 4.39 | 86.7 |
| (A) | 3.66 | 96.6 |
| (B) | 14.39 | 0. |
| (B) | 10.98 | 0. |
| (B) | 13.96 | 0. |
| (C) | 10.24 | 0. |
| (C) | 12.68 | 0. |
| (C) | 14.26 | 0. |

I claim:

1. A phosphoric acid diester of the formula:

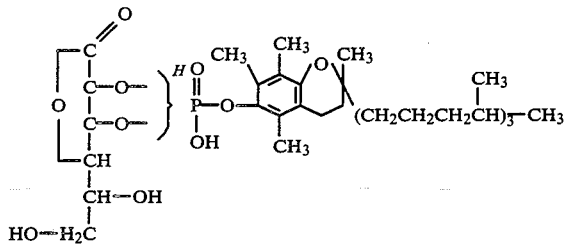

or its salt.

2. A phosphoric acid diester or its salt according to claim 1 wherein the α-tocopherol residue in the formula is DL-α-tocopherol residue.

3. A phosphoric acid diester or its salt according to claim 1 wherein the α-tocopherol residue in the formula is D-α-tocopherol residue.

4. A phosphoric acid diester salt according to claim 1 wherein the salt is potassium salt.

5. A phosphoric acid diester salt according to claim 1 wherein the salt is sodium salt.

6. A phosphoric acid diester salt according to claim 1 wherein the salt is calcium salt.

7. A process for producing a phosphoric acid diester of the formula:

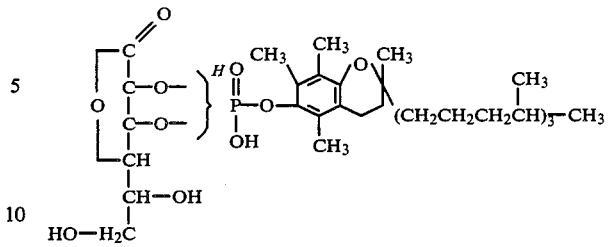

or its salt, which comprises reacting α-tocopherol with a halogenophosphorylating agent and reacting the resultant product with ascorbic acid having the hydroxy groups in the 5- and 6-positions protected with protecting groups, followed by removing the protecting groups.

8. A process according to claim 7 wherein the α-tocopherol residue in the formula is DL-α-tocopherol residue.

9. A process according to claim 7 wherein the α-tocopherol residue in the formula is D-α-tocopherol residue.

10. A process according to claim 7 wherein the halogenophosphorylating agent is phosphoryl trichloride (or tribromide) and the protecting group is an isopropylidene group.

11. A process according to claim 7 wherein the protecting groups are removed through hydrolysis under the presence of hydrochloric acid.

12. A pharmaceutical composition for the treatment of cataracts which comprises an anti-cataract effective amount of a compound of the formula:

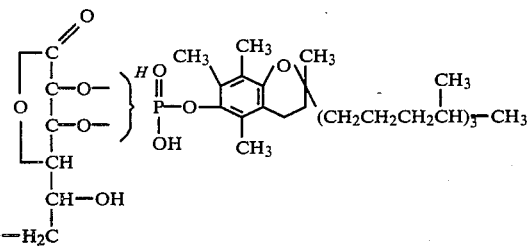

or a pharmaceutically acceptable salt thereof and a carrier.

13. A composition according to claim 12 wherein the salt is sodium, potassium or calcium salt.

* * * * *